US007452350B2

(12) United States Patent
Yeakley

(10) Patent No.: US 7,452,350 B2
(45) Date of Patent: Nov. 18, 2008

(54) PRE-DOSED ORAL LIQUID MEDICATION DISPENSING SYSTEM

(76) Inventor: Rourke M. Yeakley, 3286 N. Shadow Hills Dr., Eagle, ID (US) 83616

(*) Notice: Subject to any disclaimer, the term of this patent is extended or adjusted under 35 U.S.C. 154(b) by 207 days.

(21) Appl. No.: 10/617,166

(22) Filed: Jul. 9, 2003

(65) Prior Publication Data

US 2005/0010190 A1 Jan. 13, 2005

(51) Int. Cl.
*B67D 5/00* (2006.01)
*B67D 5/60* (2006.01)
*B65D 35/22* (2006.01)
*A61B 19/00* (2006.01)

(52) U.S. Cl. ...................... 604/416; 222/88; 222/145.5; 222/94; 433/90; 206/219; 604/87

(58) Field of Classification Search ................... 222/81, 222/82, 137, 145.5, 145.6, 88, 94; 433/90; 206/219, 222, 368, 369, 229; 604/87, 88, 604/204, 416
See application file for complete search history.

(56) References Cited

U.S. PATENT DOCUMENTS

| | | | | |
|---|---|---|---|---|
| 2,673,563 | A | 3/1954 | Kwast | |
| 2,754,590 | A * | 7/1956 | Cohen | 433/90 |
| 2,787,269 | A * | 4/1957 | Cohen | 604/416 |
| 3,302,644 | A | 2/1967 | Kennedy et al. | |
| 3,327,710 | A * | 6/1967 | De Santo et al. | 206/222 |
| 4,027,985 | A | 6/1977 | Loesser, III | |
| 4,059,109 | A * | 11/1977 | Tischlinger | 604/88 |
| 4,410,323 | A | 10/1983 | Hodosh et al. | |
| 4,457,427 | A * | 7/1984 | Cafiero | 206/229 |
| 4,548,601 | A * | 10/1985 | Lary | 604/204 |
| 4,632,244 | A * | 12/1986 | Landau | 206/219 |
| 5,037,389 | A | 8/1991 | Dooley | |
| 5,196,001 | A | 3/1993 | Kao | |
| 5,199,567 | A * | 4/1993 | Discko, Jr. | 206/369 |
| 5,286,257 | A * | 2/1994 | Fischer | 604/82 |
| 5,298,248 | A | 3/1994 | Hugyes et al. | |
| 5,593,697 | A | 1/1997 | Barr et al. | |
| 5,609,581 | A | 3/1997 | Fletcher et al. | |
| 5,761,885 | A | 6/1998 | Hansen | |
| 5,819,921 | A * | 10/1998 | Schmid | 206/368 |
| 6,200,295 | B1 | 3/2001 | Burchett et al. | |
| 6,349,850 | B1 * | 2/2002 | Cheikh | 206/222 |
| 6,386,872 | B1 * | 5/2002 | Mukasa et al. | 206/219 |

FOREIGN PATENT DOCUMENTS

| | | |
|---|---|---|
| DE | 24 57 994 | 6/1976 |
| EP | 1 163 918 | 12/2001 |
| EP | 1 308 149 | 5/2003 |
| WO | WO 98/15314 | 4/1998 |

OTHER PUBLICATIONS

International Search Report With Above-Listed Patents.

* cited by examiner

*Primary Examiner*—Kevin P Shaver
*Assistant Examiner*—Melvin A Cartagena
(74) *Attorney, Agent, or Firm*—Frank J. Dykas; Derek H. Maughan; Dykas, Shaver & Nipper, LLP

(57) ABSTRACT

A liquid oral medication dispensing system made up of an ampule configured to hold a pre-measured quantity of the selected medication and to dispense that quantity of oral medication through an opening in the ampule formed by a puncturing device. This dispensing system provides a system for storing and delivering oral medications that can be utilized in a broad variety of circumstances by individuals with little or no medical training and provides safe, effective use of the medication.

10 Claims, 3 Drawing Sheets

PRE-DOSED ORAL LIQUID MEDICATION DISPENSING SYSTEM

BACKGROUND OF THE INVENTION

1. Field of the Invention

The present invention generally relates to medication dispensing devices and more particularly to a portable disposable pre-measured medicine dispenser.

2. Background Information

One of the greatest benefits of modern medicine has been the ability of antibiotics and other medications to cure and treat diseases that have plagued mankind from the beginning of time. In generally civilized societies, individuals have access to medications whose usage can be lifesaving in many instances. While these medications exist, the availability and dispersal of these medications to individuals that truly need them throughout the world has not yet been properly established. One of the reasons for which this dispersal of medication has not been effective in all locations is that in many locations individuals do not know how much medication to impart to reach the desired dosing requirements for efficacy while also preventing damage to the individual. Another problem that occurs is that in some instances the ability to take the medication cannot be effectively performed because of a lack of dispensatory materials at the designated location.

Another problem in the prior art occurs with the storage of such medications. Many times a medication is sold in large containers or in shipments that may require refrigeration. Thus the cost of the medication itself is further increased by the cost of transporting the medication to the desired location and storing the medication. In other instances, the required amount of medicine to be administered may be so small in comparison with the quantities in which the medication is shipped and stored that purchase of the medication is cost prohibitive.

Many times, the administration of the medication requires more time, knowledge or precision than an individual is able to apply to the administration of medication. When this occurs, an individual will measure and utilize the medication inappropriately. As a result, persons may become ill from taking too much of the medication, while at other times the medication is ineffective against the disease because of improperly small dosages of the medications are administered. This in turn can lead to a variety of health issues including sickness, discomfort, pain, irritability, and even death to individuals who fail to take the proper medication at the proper times.

In addition to these problems, in treating bacterial infections, and other biological hazards including those organisms that have been employed as weapons, the improper use and dosing of antibiotics can lead to the mutation and the creation of resistant bacteria that do not respond to the traditionally outlined antibacterial regimens.

Therefore what is needed is a system for storing and dispensing pre-dosed quantities of medications that can be safely and effectively dispensed to individuals in a variety of circumstances. What is also needed is such a device wherein the medications can be safely stored and then subsequently dispensed when needed according to a selected protocol at a selected time, by an individual with little or no medical training. What is also needed is a method and device for storing and delivering pre-dosed amounts of desired medications which does not require the use of additional drug delivery devices.

Accordingly, it is an object of the invention to provide a system for storing and dispensing pre-dosed quantities of medications that can be safely and effectively dispensed to individuals in a variety of circumstances. Another object of the invention is to provide a device that can be used to safely store a medication and then to subsequently dispense that medication according to a selected protocol and at a selected time. Another object of the invention is to provide such a medicine delivery and storage system that is predosed and easy to deliver so as to allow by an individual with little or no medical training to adequately and appropriately administer the medication. Another object of the invention is to provide a method and device for storing and delivering pre-dosed amounts of desired medications in a container which can also be utilized to deliver the medication to the individual and which does not require the use of additional drug delivery devices.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention is a liquid medication dispensing system for dispensing measured doses of selected medications comprising an ampule containing a pre-selected quantity of a selected medication. The ampule is configured to hold a pre-measured quantity of the selected medication and to dispense that quantity of medication through an opening in the ampule formed by a puncturing device. These medications can be stored within the ampule in either a suspended solution or in a powdered form separated from a liquid reconstituting agent by a rupturable membrane. These medications are held in capsules that can be activated, mixed and then punctured by a puncturing device. The puncturing device being of a calibrated size and formed as a part of a storage container, which is configured to hold the ampule in a desired position and orientation. In the preferred embodiment, the ampule may have a handle attached to it so as to prevent the placement of increased pressure upon the medicine containing portions of the ampule and to ensure the delivery of the proper quantity of material out of the device.

The present invention is stored as a kit containing at least one ampule having a designated predosed quantity of medication, being stored within a sealed container. The sealed container having a portion configured to define at least one puncturing device. To use the device the container is opened the ample removed, agitated or mixed according to the manufacturers directions and then punctured by the puncturing device. Once the ampule has been punctured, the ampule can be squeezed so as to expel the predosed quantity of medication out of the device and to deliver this medication to the intended beneficiary.

This dispensing system provides a variety of advantages over the prior art and provides a system for long-term storage of dosing medications, particularly oral and topical medications that can be utilized in a broad variety of circumstances by individuals with little or no medical training and which will provide safe, effective use of the medication which will thus provide designated healing properties.

Further, the purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measure by the claims, nor is it intended to be limiting as to the scope of the invention in any way.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1A:
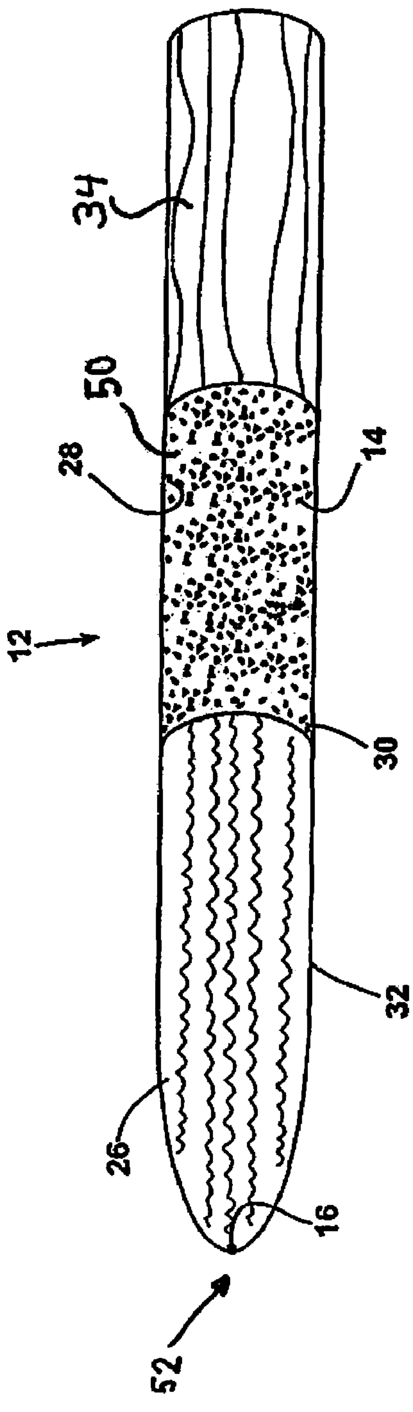
FIG. 1A is a detailed top view of a first embodiment of an ampule of the present invention.
Figure 1B:
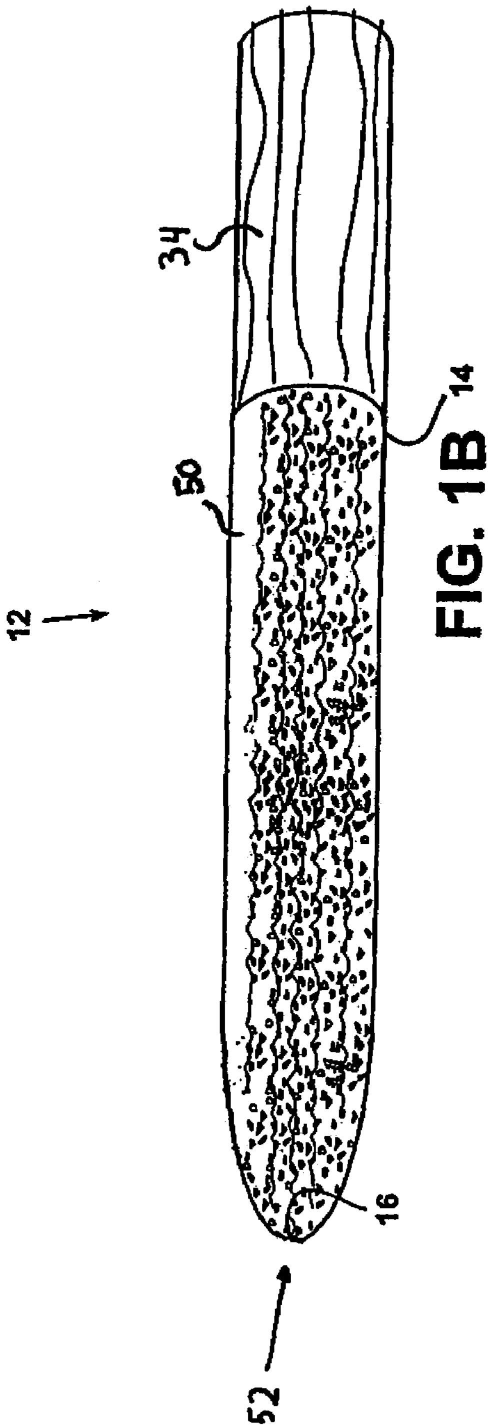
FIG. 1B is a detailed top view of a second embodiment of an ampule of the present invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Referring now to FIGS. 1-4 the present invention of a system for dispensing measured dosages of selected medications is shown. The principal element in the system is an ampule. Examples of the ampules utilized in the preferred embodiment of this invention is shown in FIGS. 1A and 1B. These ampules 12 are configured to contain and dispense measured dosages of selected medications. FIG. 1A shows an ampule 12, which contains a desired amount of a medication 14 therein. FIG. 1B shows an ampule 12 wherein the medication is reconstituted to and is ready for delivery. In FIG. 1A the medication 14 is in a dry powdered form and is separated from a reconstituting liquid 32 by a rupturable membrane 30. This rupturable membrane 30 divides the ampule 12 into a medication chamber 28 and a reconstituting chamber 26.

In order to use the device the ampule 12 is removed from a stored location, shaken or mixed to resuspend the medication into a solution. The ampule 12 is then punctured, preferably near an end portion 52 of the ampule 12. When this occurs, an aperture or opening 16 is formed within the ampule 12. By squeezing the ampule 12, the medication is pushed out of the opening 16 and can be delivered to the individual requiring the medication. In the preferred embodiment, the ampule 12 further comprises a handle portion 34 which prevents excess pressure from being applied to the ampule 12 when the device is being punctured.

In the embodiment shown in FIG. 1A, the medication 14 is stored as a powder and the reconstituting liquid 32 is held in a separate chamber 26 by a rupturable membrane 30. Therefore, in order for the reconstituting liquid 32 and the medication 14 to be mixed, the membrane 30 must be ruptured. In order to rupture this membrane the ampule 14 must be bent so as to produce sufficient pressure against the membrane 30 so as to cause the membrane 30 to break and for the liquid 32 and the medication 14 to be mixed. This mixing is enhanced by shaking or agitating the ampule 12.

Once the medication 14 and the liquid 32 have been mixed, the ampule 12 can then be punctured by a puncturing device to produce an opening 16 sufficient in size to allow delivery of the medication to the intended recipient. Once the opening 16 has been made in the ampule 12, the medication may be delivered by simply squeezing the ampule 12 to force the medication out of the ampule 12 through the opening 16.

In the preferred embodiment, the expulsion of medication through the opening 16 is enhanced by the inclusion of a quantity of an expelling material 50. In the preferred embodiment this is simply a quantity of air that is included within the ampule 12 and is configured to increase the efficacy of expelling material out of the ampule 12. Depending upon the specific medications that are utilized, an additional rupturable membrane 30 may be required to separate the expelling material 50 from the remainder of the medications that are held in the ampule.

Typically, this system is utilized with oral drug delivery, however it is to be distinctly understood that this disclosure is not limited thereto but may also be utilized with other types of drug delivery products.

Figure 2:
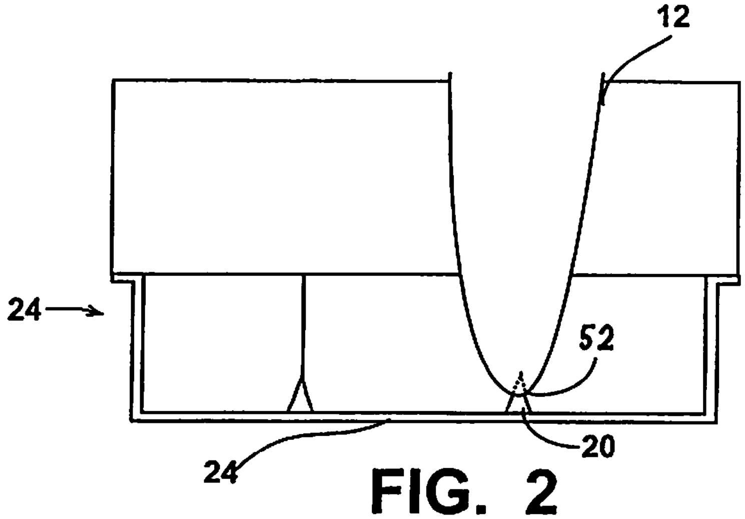
FIG. 2 is a detailed side view of one an ampule in contact with a puncturing device.

Referring now to FIG. 2, a detailed end view of an embodiment of the invention is shown. In this embodiment, an ampule 12 is shown in a position against a puncturing device 20. The puncturing devices 20 are formed within a bottom portion 24 of a storage container 22. Which is typically made of a hardened type of plastic however it is to be understood that the invention is not limited to such a type of material but that the storage container may also be variously configured to be made of a variety of other types of materials. In addition to placing the puncturing devices within the bottom portion of the device it is to be distinctly understood that the invention is not limited thereto but may be variously embodied. The puncturing devices 20 may be individual devices that are included within the container upon storage or may be included as a portion of the side wall or even the top of the container 22. In addition, in other embodiments the puncturing device may be included as a sheathed portion or end that is configured to connect with the ampule.

The puncturing devices 20 are calibrated so as to form an opening 16 having a designated size within the ampule 12. These openings 16 are also configured to allow designated amounts of liquid to be passed through the device at a designated time. This storage container 22 is also configured to hold the ampules 12. Views of the storage containers and the combination of the storage container and the ampule 12 are shown in FIGS. 3 and 4.

Figure 3:
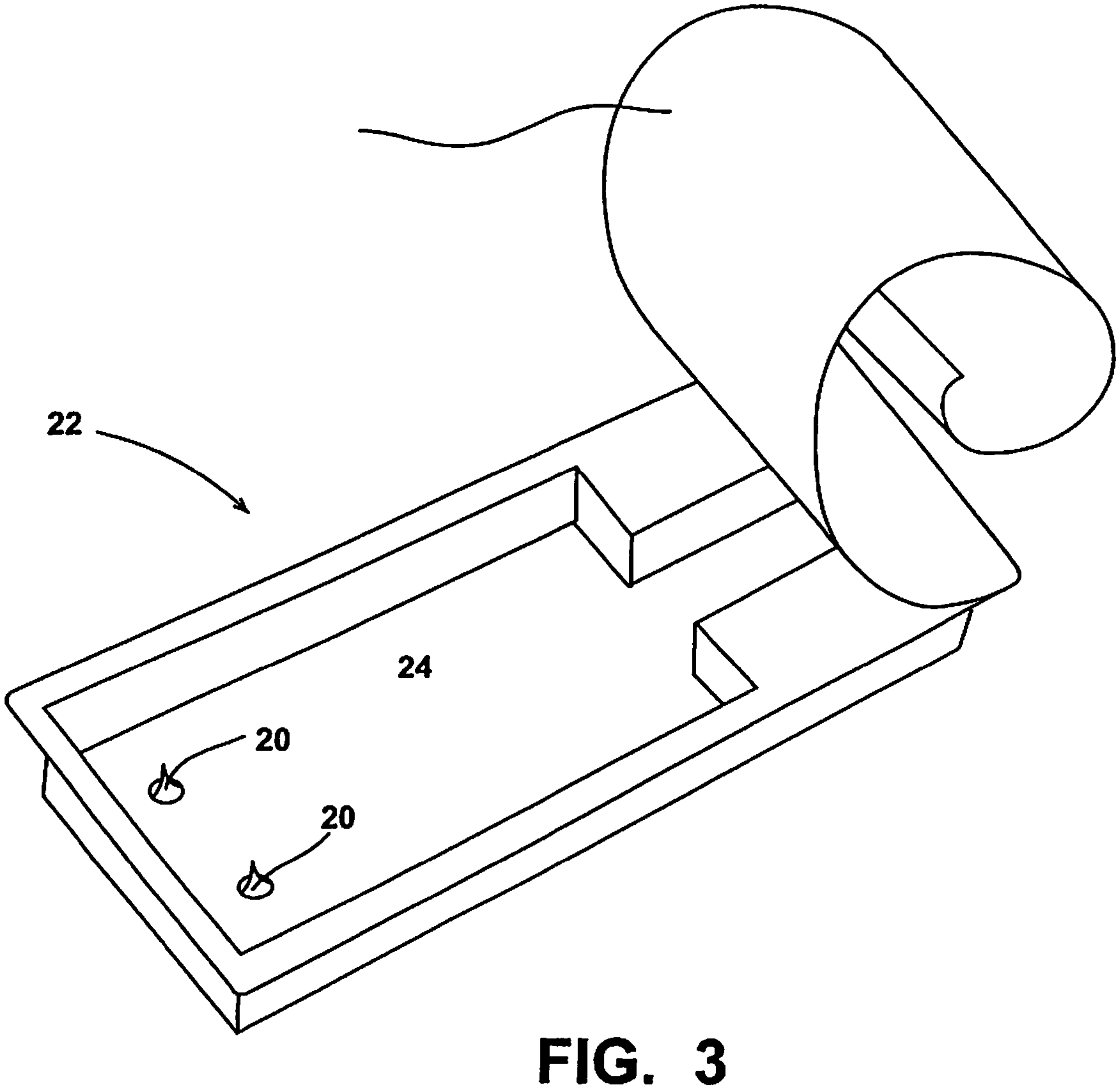
FIG. 3 is a top perspective view of the container of the present invention.

Referring now to FIG. 3 a top perspective view of the container 22 used in the present invention is shown. The container 22 of the present invention is made up of bottom portion that is configured to hold an ampule 12 therein. The bottom portion 24 of the container 22 is configured to form puncturing portions 20 which as discussed previously are configured to create openings of a designated size within the ampule 12. The container has a top portion 38 that is configured to be peeled away so as to reveal the contents of the inner portion of the container 22. While in this configuration the top portion 38 is configured to be peeled away it is to be distinctly understood that the present invention is not limited to a peel back style top portion 38 but may also be variously embodied to include a variety of other types of closures.

Figure 4:
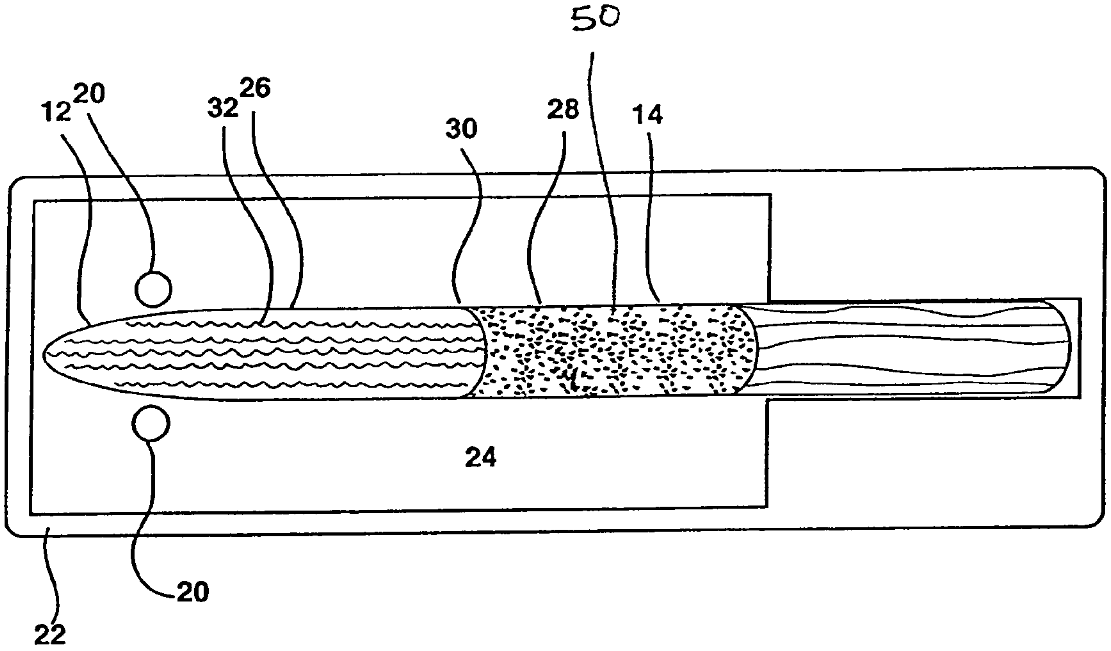
FIG. 4 is a top plan view of the present invention wherein the cover of the container has been removed

FIG. 4 shows the placement of an ampule within a container as the device would be typically held during storage.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

I claim:

1. An oral liquid medication dispensing system for dispensing measured dosages of selected oral medications comprising:

a puncturable, compressible ampule having a closed body containing a pre-selected quantity of a selected liquid oral medication therein, said ampule configured to hold a premeasured quantity of said selected medication, and to dispense said quantity of medication through an opening in said ampule after said opening is formed within said ampule and a designated quantity of pressure is applied to said ampule, and a calibrated puncturing device configured to create an opening of a desired size within said ampule, and a designated quantity of an expelling material, said ampule configured to laterally compress when a designated quantity of pressure is applied to said ampule and to force said expelling material and said medication out of said ampule through said opening.

2. The oral liquid medication dispensing system of claim 1 wherein said expelling material is air.

3. The oral liquid medication dispensing system of claim 2 further comprising a container configured to hold said ampule and said puncturing device, in a sealed environment.

4. The oral liquid medication dispensing system of claim 3 wherein said puncturing device is a portion of said container.

5. The oral liquid medication dispensing system of claim 4 wherein said container is a generally rectangularly shaped box configured to hold said ampule therein, said container having a bottom portion said bottom portion defining at least one puncturing device therein.

6. A self-contained dispensing system for dispensing measured amounts of oral medication stored in a powdered form but delivered in a liquid form, said system comprising:

a closed, squeezable, puncturable ampule having a first chamber configured to hold a premeasured amount of a selected medication stored in a powdered form therein, and a second chamber configured to hold a premeasured amount of a reconstituting liquid therein, said first chamber separated from said second chamber by a pressure sensitive breakable membrane, said membrane configured to be broken when a preselected quantity of pressure is applied to the membrane thus allowing said powder to be mixed with said reconstituting liquid and for said powder to be suspended within said reconstituting liquid and to allow said suspension to be dispensed from said ampule through an opening of a calibrated size located within said ampule when pressure is applied to said ampule; and a calibrated puncturing device, said calibrated puncturing device configured to produce a hole of a calibrated size within said ampule; and a designated quantity of an expelling material, said ampule configured to compress when a designated quantity of pressure is applied to said ampule and to force said expelling material and said medication out of said ampule.

7. The oral medication dispensing system of claim 6 wherein said expelling material is air.

8. The oral medication dispensing system of claim 6 further comprising a container configured to hold said ampule and said puncturing device, in a sealed environment.

9. The oral medication dispensing system of claim 8 wherein said puncturing device is a portion of said container.

10. The oral medication dispensing system of claim 8 wherein said container is a generally rectangularly shaped box configured to hold said ampule therein, said container having a bottom portion said bottom portion configured to contain at least puncturing device therein.

* * * * *